United States Patent
Lenzenhuber et al.

(10) Patent No.: US 11,969,299 B2
(45) Date of Patent: Apr. 30, 2024

(54) TOOL HAVING A WORKING END DETERMINING DEVICE IN THE SHAFT REGION

(71) Applicant: Aesculap AG, Tuttlingen (DE)

(72) Inventors: Frederick Lenzenhuber, Tuttlingen (DE); Andre Bürk, Villingen-Schwenningen (DE)

(73) Assignee: Aesculap AG, Tuttlingen (DE)

( * ) Notice: Subject to any disclaimer, the term of this patent is extended or adjusted under 35 U.S.C. 154(b) by 413 days.

(21) Appl. No.: 17/285,173

(22) PCT Filed: Oct. 18, 2019

(86) PCT No.: PCT/EP2019/078453
§ 371 (c)(1),
(2) Date: Apr. 14, 2021

(87) PCT Pub. No.: WO2020/079268
PCT Pub. Date: Apr. 23, 2020

(65) Prior Publication Data
US 2021/0378779 A1 Dec. 9, 2021

(30) Foreign Application Priority Data
Oct. 18, 2018 (DE) .................... 10 2018 125 884.4

(51) Int. Cl.
*A61B 90/00* (2016.01)
*A61B 17/00* (2006.01)
*A61B 90/98* (2016.01)

(52) U.S. Cl.
CPC .............. *A61B 90/08* (2016.02); *A61B 17/00* (2013.01); *A61B 90/98* (2016.02); *A61B 2017/00221* (2013.01); *A61B 2090/0806* (2016.02)

(58) Field of Classification Search
CPC ......... A61B 90/08; A61B 90/98; A61B 17/00; A61B 2090/0806; A61B 2017/00221
(Continued)

(56) References Cited

U.S. PATENT DOCUMENTS 7,431,682 B2 * 10/2008 Zeiler .................... B24B 23/00
83/72
7,722,531 B1 5/2010 Boche
(Continued)

FOREIGN PATENT DOCUMENTS

DE         20012237 U1     10/2000
DE      102006057338 A1     6/2008
(Continued)

OTHER PUBLICATIONS

Written Opinion received in Application No. PCT/EP2019/078453 dated Apr. 30, 2020, with translation, 10 pages.
(Continued)

*Primary Examiner* — Zhen Y Wu
(74) *Attorney, Agent, or Firm* — Christopher A. Rothe; Culhane Meadows PLLC (57) ABSTRACT

A tool includes a working end determining device arranged in a shaft region or gripping region thereof for determining and/or detecting a working end of the tool. The working end determining device includes a writable and/or readable data storage device that stores data relating to the working end of the tool. The working end determining device provides data externally with reference to the working end of the tool for detecting the working end of the tool. The working end determining device can be a communication device that includes the data storage device and an antenna device. Alternatively, the working end determining device can be a unit integrated into the tool that is connected to an external control device via an electrical contacting. The integrated
(Continued)

unit includes a resistor determining the working end of the tool and/or a storage device storing data with respect to the working end.

9 Claims, 8 Drawing Sheets

(58) Field of Classification Search
USPC .......................................................... 40/568
See application file for complete search history.

(56) References Cited

U.S. PATENT DOCUMENTS

| | | | |
|---|---|---|---|
| 9,622,832 B2* | 4/2017 | Birkenbach | A61B 90/98 |
| 10,350,024 B2 | 7/2019 | Kube et al. | |
| 10,624,653 B2* | 4/2020 | Chien | A61B 17/1626 |
| 10,709,945 B2 | 7/2020 | Hunter | |
| 2004/0092991 A1 | 5/2004 | Deng | |
| 2006/0047271 A1* | 3/2006 | McPherson | A61B 17/32 |
| | | | 606/1 |
| 2006/0159533 A1* | 7/2006 | Zeiler | B25D 17/00 |
| | | | 408/226 |
| 2006/0214791 A1* | 9/2006 | Tethrake | A61B 90/98 |
| | | | 340/572.1 |
| 2007/0115130 A1* | 5/2007 | Eveland | H01Q 9/28 |
| | | | 343/700 R |
| 2008/0122404 A1* | 5/2008 | Brotto | B25F 5/00 |
| | | | 320/114 |
| 2008/0177267 A1 | 7/2008 | Sands et al. | |
| 2008/0211634 A1* | 9/2008 | Hopkins | H04N 23/54 |
| | | | 348/E5.043 |
| 2008/0262526 A1* | 10/2008 | Neubardt | A61B 17/1615 |
| | | | 606/180 |
| 2008/0302549 A1* | 12/2008 | Zeiler | B23B 51/00 |
| | | | 408/239 R |
| 2009/0157071 A1* | 6/2009 | Wham | A61B 18/1442 |
| | | | 606/51 |
| 2009/0201154 A1* | 8/2009 | Bauchot | G01C 15/04 |
| | | | 340/568.1 |
| 2009/0254077 A1* | 10/2009 | Craig | A61B 18/1206 |
| | | | 606/33 |
| 2011/0087605 A1* | 4/2011 | Pond | G06Q 30/012 |
| | | | 433/119 |
| 2011/0245833 A1 | 10/2011 | Anderson | |
| 2014/0048605 A1* | 2/2014 | Gatling | B25B 15/001 |
| | | | 235/492 |
| 2014/0131454 A1 | 5/2014 | Weisshaupt et al. | |
| 2015/0036127 A1 | 2/2015 | Konomura et al. | |
| 2015/0303996 A1* | 10/2015 | Calderoni | H04B 5/79 |
| | | | 307/104 |
| 2016/0262847 A1* | 9/2016 | Rickert | A61C 1/12 |
| 2017/0156710 A1* | 6/2017 | Walton | H05K 7/02 |
| 2017/0172701 A1 | 6/2017 | Kube et al. | |
| 2017/0258551 A1* | 9/2017 | Smith | G16H 40/20 |
| 2018/0256287 A1 | 9/2018 | Bosisio et al. | |

FOREIGN PATENT DOCUMENTS

| | | |
|---|---|---|
| DE | 102011052501 A1 | 2/2013 |
| DE | 102015111757 A1 | 9/2016 |
| DE | 102015016233 A1 | 6/2017 |
| EP | 1746530 B1 | 1/2007 |
| EP | 3182337 A1 | 6/2017 |
| JP | 200977965 A | 4/2009 |
| JP | 2016105265 A | 6/2016 |
| JP | 2017525398 A | 9/2017 |

OTHER PUBLICATIONS

International Search Report received in Application No. PCT/EP2019/078453 dated Apr. 30, 2020, with translation, 7 pages.
Search Report received in German Application No. 10 2018 125 884.4 dated Jun. 26, 2019, with translation, 14 pages.
Office Action received in Japanese Application No. 2021-521181 dated Sep. 8, 2023, with translation, 5 pages.

* cited by examiner

TOOL HAVING A WORKING END DETERMINING DEVICE IN THE SHAFT REGION

CROSS-REFERENCE TO RELATED APPLICATION(S)

This application is the United States national phase entry of International Application No. PCT/EP2019/078453, filed Oct. 18, 2019, and claims the benefit of priority of German Application No. 10 2018 125 884.4, filed Oct. 18, 2018. The contents of International Application No. PCT/EP2019/078453 and German Application No. 10 2018 125 884.4 are incorporated by reference herein in their entireties.

FIELD

The invention relates to a tool or instrument, and in particular relates to a medical/surgical tool or medical/surgical instrument configured to provide automatic and/or automatically documenting determination of working ends and/or recognition of working ends.

BACKGROUND

Up to now, for example, in the field of non-medical, electric hand-held machine tools, a device for automatic recognition of tool-specific data of exchangeable tools inserted into the hand-held machine tool is known, in which a tool such as a cutting drill, a chisel or the like has a geometric coding, for example a mechanical coding in the form of coding steps, in the region of an insertion shaft. By means of a reading device, such as an electronic, optical or mechanical sensor, installed in the tool accommodation and directed towards the coding, signals corresponding to the coding are generated and transmitted to a control unit of a machine tool for further processing.

In the case of tools and/or instruments found in particular in the medical field, such as hand tools, three sections are essentially distinguishable: a handle section, a shaft section, and at least one working end/effector. The shaft section connects the handle section to the working end of the tool. The working end is opposite the handle section at the other end of the tool, is the actually functional part of the tool, and may be shaped in a variety of ways specific to the application.

Tools of the type referred to here include tools generally usable in the field of medicine, instruments, spray nozzles, RF tips, ultrasonic blades, and the like. However, there is no limitation to products of the aforementioned type from the medical field in particular.

In the field of medicine, due to the type of tools and/or instruments used as well as the conditions of the respective working environments, a coupled code recognition as mentioned above is neither feasible nor practical, but instead labels or stickers are used, which can be arranged on the tool itself or also on an outer packaging of the tool. In order to recognize, for example, which tool is plugged in, the label of the tool or of each individual tool or its outer packaging has to be inspected. Up to now, there has been no automatic and/or automatically documenting determination of the working end or recognition of the working end, so that a user or customer has to recognize which product/working end it is on the basis of labels or inscribing labels, or can only recognize this on the basis of these labels, and then has to document this manually.

This adversely affects users as well as retailers or customers and manufacturers of such tools. Among other things, a user or customer of such a tool, for example, cannot readily identify whether an intended tool is suitable for his specific application or not without viewing the label or outer packaging. For example, a retailer or customer generally cannot determine which product stocks are still at a warehouse or consignment store without taking inventory. For example, a manufacturer cannot determine which products have been combined and/or used, cannot track overloading of tools and any associated product damage, and cannot provide customized logistics for a customer.

There is therefore a need (not only, but especially in the field of medicine or medical technology) for automatic recognition of tools and/or instruments, spray nozzles, HF tips, ultrasonic blades and the like, by means of which the aforementioned disadvantages can be eliminated and associated problems can be solved.

SUMMARY

The invention is therefore based on the object to provide a tool, such as a medical tool, whose proximal working end can be recognized during, for example, an insertion process (into a handpiece, handle). In addition, it should be possible to display data, for example data relating to the working end and/or further data beyond this to a user or customer or to transmit this data to the user or customer.

According to the invention, this object is solved by a tool having the features of claim 1. Advantageous further developments of the invention are the subject matter of the accompanying dependent claims.

The invention is based on the general idea of arranging a (recognition, identification, communication) device on a tool, in particular a medical (drilling, milling, screwing) tool, which permits determination or recognition of a working end (or tool) inserted in a handpiece/handle/drive unit in each case, as well as transmission of further, optionally previously written data on a data carrier and/or in a memory device, i.e. recognition of a working end in conjunction with a readable data memory (using a communication device with low power consumption based on, for example, technology marketed under the federally registered trademark BLUETOOTH®, RFID, NFC and the like) together with the working end.

For this purpose, the invention provides that a device determining the working end of the tool is provided thereon with at least one data storage device or a data storage area of a predetermined data storage capacity, wherein data stored in the data storage is related to the working end in such a way that it determines the working end and/or can be used to recognize it, and wherein, in addition, the data storage can hold further data, for example application-related or process-related data and the like. Preferably, the device is a communication device with low power consumption, with which devices can be networked or wirelessly transmit and/or exchange data in a communication range of typically a few meters up to a few 10 meters. Further preferably, the communication device may be a device marketed under the federally registered trademark BLUETOOTH® or RFID device. Alternatively, the invention provides for providing a resistor and/or a storage device integrated in the tool, wherein the resistor is designed or specified for a determination of the working end, and the storage device can hold further data, for example application-related or process-related data and the like.

Application-related, product-related or process-related data can be, for example, an article number and/or a graphic representation of the article, a LOT specification, i.e. information about a compiled batch of a particular product, an BBD or best-before date and the like.

With such application-related or process-related data, a user or customer in conjunction with a data processing device is enabled to document uses in a variety of ways. For example, a display device, such as a display of an external device or of portable computer, tablet, smartphone, or a different terminal device, can show the customer what product it is. Furthermore, inventory-related information can be displayed to the user or customer and/or an automatic replenishment order can be triggered when the inventory level is below a pre-determinable number (message, for example, "Your consignment stock is about to be exhausted. Calculated on the consumption of the last four weeks, a requirement of 50 pieces will be delivered to you. Tracking ID: 123456, delivery by delivery service"), the user or customer can be informed of an undesirable condition and can be guided in favor of an improvement (message, for example, "Caution: handpiece overload detected. Contact pressure too high. Please use another working end if possible"), or diagnostic information can be provided to the user or customer (message, for example, "Handpiece overload detected. The working ends used during the recording period were type A, type B, . . . X times excessive current consumption was detected" (X can be a numerical number here)). In addition, direct logging of used components in analog and/or digital form, for example in an IT infrastructure with, for example, storage space, computing power and/or application software locally and/or via the Internet (cloud), in decentralized databases, in server structures or the like, and/or in a patient file is also representable.

According to the invention, this advantageously results in a direct, automated tool recognition for a user, customer and/or manufacturer, a transferability of any number of further data to a user, customer and/or manufacturer, and the possibility of immediately writing into, for example, an electronic patient file for a user or customer.

In detail, the object is solved by a tool having a working end determining device arranged in a shaft area thereof for determining a working end of the tool, wherein the working end determining device includes a writable and/or readable data storage device configured to store in at least a first memory area at least data related to the working end of the tool, and wherein the working end determining device is arranged to provide in an externally detectable manner the data related to the working end of the tool for recognizing the working end of the tool.

Preferably, the working end determination device is a communication device with low power consumption comprising at least the data storage device and an antenna device.

Also preferably, the communication device with low power consumption is housed in a hollow body arranged at a handle or shaft end of the tool opposite the working end so as to extend the handle or shaft end.

Further preferably, the low power consumption communication device is embedded in a handle or shaft end of the tool opposite the working end.

Alternatively, the communication device with low power consumption is preferably accommodated in a ring body surrounding a shaft section or a handle section.

Advantageously, the antenna device may be coil-shaped in the ring body housing the communication device with low power consumption, and/or the ring body housing the communication device with low power consumption may be formed as an overmolded and/or molded assembly.

Alternatively preferred, the communication device with low power consumption is arranged in an annular shape on an outer ring of a bearing device arranged on the tool, wherein the writable and/or readable data storage device is arranged on a first partial section of the outer ring of the bearing device, and the antenna device is arranged on a second partial section of the outer ring of the bearing device, and wherein the antenna device is coil-shaped. It is particularly advantageous in this case that the outer ring of the bearing device is held stationarily and therefore does not rotate with it, so that no vibrations are to be expected due to any imbalance and the like.

Alternatively preferred, the communication device with low power consumption is housed in a sleeve-shaped or ring-shaped spacer forming a carrier element for positioning on an outer circumference of the tool, wherein the writable and/or readable data storage device is arranged in a first partial section of the spacer, and the antenna device is arranged in a second partial section of the spacer, and wherein the antenna device is coil-shaped.

Alternatively preferred, the communication device with low power consumption is housed in an element forming a splash guard on an outer circumference of the tool, wherein the writable and/or readable data storage device is arranged in a first partial section of the splash guard element, and the antenna device is arranged in a second partial section of the splash guard element, and wherein the antenna device is coil-shaped.

Advantageously, the element forming the splash guard can be a splash guard body for a bearing device arranged on the tool.

Furthermore, advantageously and preferably, the communication device with low power consumption may be an RFID device or a device marketed under the federally registered trademark BLUETOOTH® LE.

Furthermore, alternatively preferred, the working end determining device is a unit integrated into the tool, which can be connected to an external control device via an electrical contact in a handpiece region of the tool.

Advantageously, the unit integrated into the tool can comprise a resistor determining the working end of the tool and/or a storage device storing data related to the working end.

Preferably, the unit integrated into the tool extends into the tool starting from an end of the tool on the handle side or shaft side with a channel-shaped structure in the direction of the working end, wherein the resistor determining the working end of the tool and/or the storage device storing data related to the working end is arranged in the channel-shaped structure at a first end facing the working end, and the electrical contact is arranged at a second end facing away from the working end, wherein at least one conductive section electrically contacts the resistor and/or the storage device, and wherein the channel-shaped structure is enclosed by an insulator and is electrically insulated by the latter with respect to the tool.

In this regard, advantageously, the writable and/or readable data storage device may include at least one second memory area configured to store predetermined data other than the data stored in the at least one first memory area, which is the data related to the working end of the tool.

BRIEF DESCRIPTION OF THE DRAWING FIGURES

The invention is described in more detail below with reference to the accompanying drawings that are described below.

FIG. 8b shows a truncated cross-sectional view of the working end determination device of FIG. 8a;

DETAILED DESCRIPTION

Figure 1:
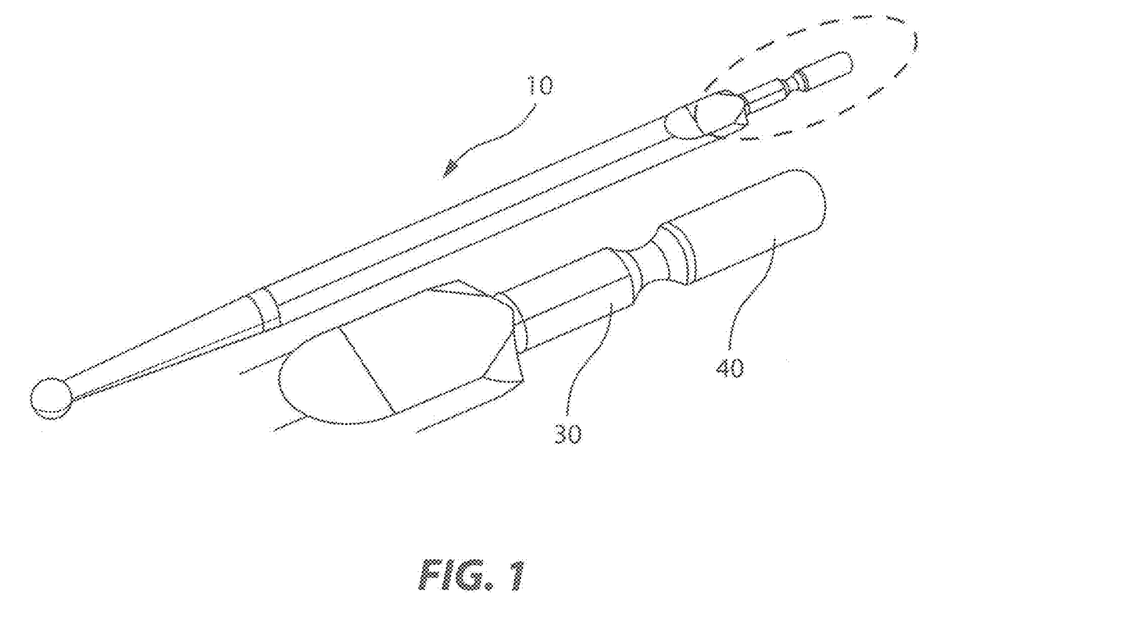
FIG. 1 shows a schematic representation of a tool with a working end determination device according to a first configuration example of the present invention.

FIG. 1 shows a schematic representation of a tool with a working end determination device according to a first configuration example.

In the figures, identical reference signs designate identical or at least equivalent parts and components. Expediently, a repeated, redundant description of such parts and components is omitted in this respect.

A working end determination device in this context means a device arranged on a tool, for example a tool for medical purposes such as a drilling, milling or screwing tool that can be rotatably inserted into a drive handpiece, for determining or recognizing at least a working end of the (medical) tool. A working end recognition device is therefore in this respect synonymous with or has the same meaning as the working end determination device. For this purpose, the working end determination device holds, stores or contains data determining the working end of the tool, i.e. data related to the working end of the tool, and is configured to output or signal this data in an externally detectable manner to outside the tool in such a way that an external device communicatively connected to the working end determination device can detect the working end located at the tool based on the output data or signaling. Furthermore, the working end determination device is configured to store, in addition to the data relating to the working end, further data, for example application-related, product-related or process-related data, and also to output them to the external device as required.

Application-related, product-related or process-related data as mentioned above can be, for example, an article number and/or a graphical representation of the article, a LOT indication, i.e. information about a compiled batch of a particular good, a BBD or best-before date and the like.

With such application-related or process-related data, a user or customer, in conjunction with a data processing device, is enabled to document uses in a variety of ways. For example, a display device, such as a display of an external device of a portable computer, tablet, smartphone, virtual reality, augmented reality, or a different terminal device, can show the customer what product it is. Furthermore, inventory-related information can be displayed to the user or customer and/or an automatic replenishment order can be triggered when the inventory level is below a pre-determinable number (message, for example, "Your consignment stock is about to be exhausted. Calculated on the consumption of the last four weeks, a requirement of 50 pieces will be delivered to you. Tracking ID: 123456, delivery by delivery service"). Or, the user or customer can be informed of an undesirable condition and can be guided in favor of an improvement (message, for example, "Caution: handpiece overload detected. Contact pressure too high. Please use another working end if possible"). Or, diagnostic information can be provided to the user or customer (message, for example, "Handpiece overload detected. The working ends used during the recording period were type A, type B, . . . X times excessive current consumption was detected"). In addition, it is also possible to directly log the components used in a patient file, for example.

In the present first configuration example, the transmission, i.e., the output of respective ones of the aforementioned data, is performed using a communication (or communication device or communication method), based, for example, on a transmission technology or radio technology with low power consumption, with which devices can be networked or can wirelessly transmit and/or exchange data in a near-field environment, typically in a communication range of a few meters up to 10 meters. Examples of such a transmission technology are technologies marketed under the federally registered trademarks BLUETOOTH®, BLUETOOTH® LE (BLE for short) and BLUETOOTH SMART® as an extension complementing the industry standard marketed under the federally registered trademark BLUETOOTH®, RFID or NFC. In this configuration example, communication components of the transmission technology with low power consumption, such as BLUETOOTH® LE brand components or an RFID device, for example an RFID chip or transponder or tag with predetermined data storage capacity, are thereby housed and arranged in the working end determination device. A respective device further comprises at least one antenna for wireless transmission of the data. BLUETOOTH® brand technology per se is well documented, so further details are not redundantly described herein.

In this context, an RFID device is understood to be a radio frequency identification device (RFID=Radio Frequency Identification). A wide variety of information can generally be stored on an RFID chip, and a reading device can read this data or information at any time via radio. Near field communication (NFC) in devices such as smartphones and the like is a special version of RFID.

RFID chips or transponders usually contain a microchip, an antenna, preferably in the form of a coil, with a diameter depending on a range to be achieved, a carrier or housing to protect the transponder electronics from the environment, and in the case of active RFID chips, an energy source, for example a battery. In passive RFID chips, energy is supplied externally via the antenna, i.e. RFID/NFC can operate passively and does not require a battery or other power supply, but can be supplied with energy from a wave emitted by a scanner on a radio frequency, storing it in a small capacitor and thus supplying power to a microcontroller on the chip. Data can be transmitted to the scanner using what is known as load modulation, in which a field of the scanner is loaded more or less heavily, wherein these load variations can be registered by the scanner as serial data, or using the principle of "modulated backscatter", in which spurious frequencies are backscattered by the scanner in a way that can be interpreted as digital data.

The available storage capacity of the writable memory of an RFID chip can range from a few bits to several Kbytes. The dataset of the transponder is permanently stored in it as a running unique number (inherent identity) when it is manufactured or as non-unique data when it is applied. Tags available in the meantime can also be changed later or written with further data. For this purpose, writable transponders can use non-volatile memories as memory technologies, in which data is retained without a power supply and which are therefore preferably suitable for inductively powered RFID, such as EEPROM or FRAM, and/or volatile memories, which require an uninterrupted power supply to retain the data, such as SRAM.

RFID is well documented in the prior art and is therefore not further described herein. However, it is understood that RFID as used herein is not limited to the preceding exemplary configurations and designs.

The following description of configuration examples refers to respective embodiments using an RFID device as a communication device with low power consumption. However, there is no limitation to this. It is to be understood that instead of the RFID device, a BLUETOOTH® brand device, for example a BLUETOOTH® LE brand device, or another communication device with predeterminable low power consumption can be used.

FIG. 1 illustrates, as a first configuration example, an embodiment with readable data memory in which an RFID device (not shown) is arranged on a tool 10, preferably a milling tool with a distal milling head, a tool shaft and a proximal insertion end portion at an end (insertion end portion) of the shaft portion or handle (insertion) portion 30 remote from the working end (milling head), i.e., on the shaft end side or handle side.

The insertion end portion has a non-circular profile for torque introduction/transmission into the tool shaft. The RFID device is arranged proximally to the portion with the non-circular profile in such a way that it is located outside the torque transmission traction and thus remains torque-unloaded.

In the first configuration example, the RFID device with antenna (not shown) and transponder electronics (not shown) is installed and housed in, for example, a housing 40 open on one side, which may have a round tuber shape ("ampoule-shaped"), and the housing 40 is preferably suitably hinged/fixed/formed in one piece of material on the proximal end of the tool 10 in a fluid-tight and gas-tight manner.

Figure 2:
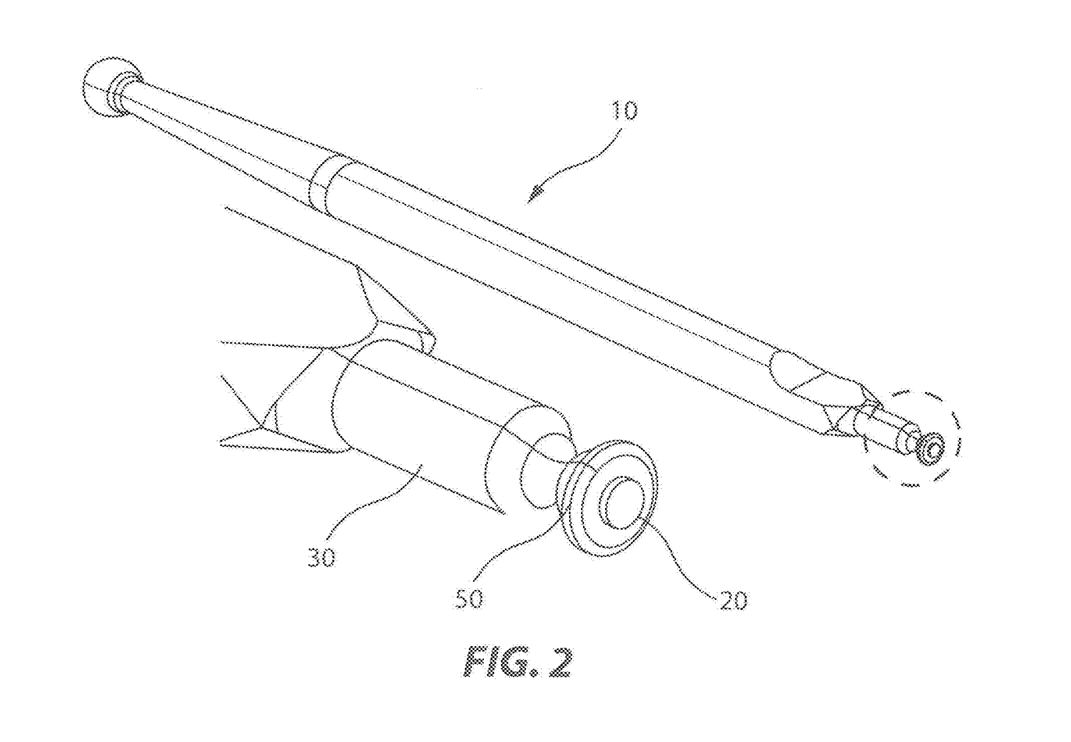
FIG. 2 shows a schematic representation of a tool with a working end determination device according to a second configuration example of the present invention.

FIG. 2 also illustrates, as a second configuration example, an embodiment with readable data memory, in which the RFID device 20 is embedded, i.e. countersunk into the tool, into a recess forming a kind of housing interior on the tool 10 at a proximal end of the shaft section or handle section 30 remote from the working end, i.e. on the shaft end side or handle side. In the second configuration example, the RFID device 20 with antenna (not shown) and transponder electronics (not shown) is housed in, for example, the recess, which can be open on one side and can be designed with a cover element sealing the opening in a fluid-tight and gas-tight manner, and the recess is preferably hinged/fixed in a suitable manner and shape, for example as a grip-friendly, round extension 50 with approximately the diameter of the tool at the hinge location on the tool end side.

It should be noted at this point that the extension 50 according to FIG. 2 is only shown schematically and of course has to be adapted to the RFID device housed in its recess, at least with regard to its axial dimensions.

Figure 3:
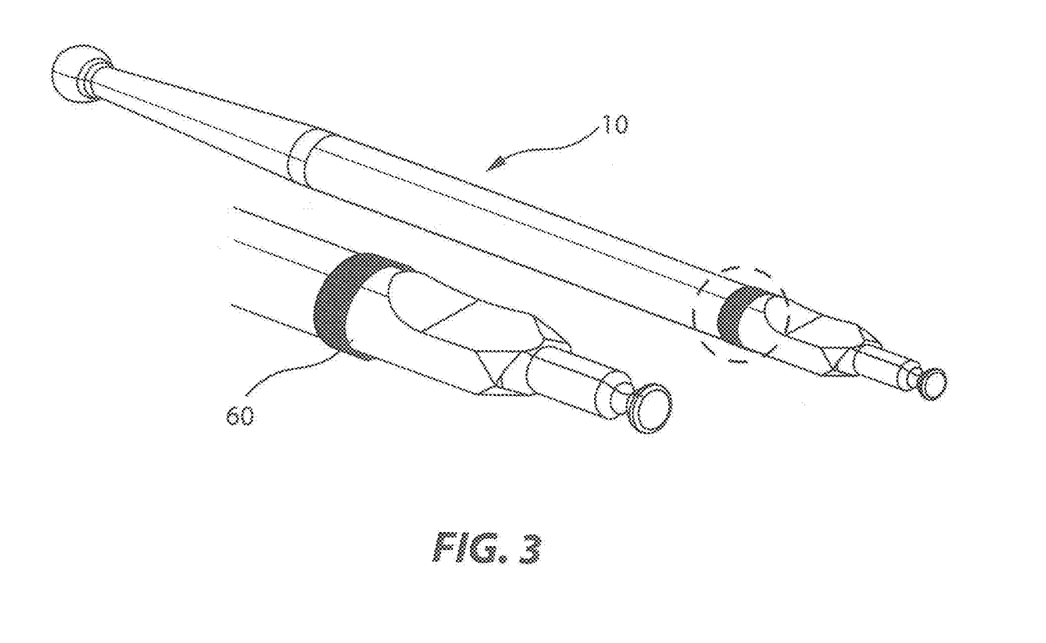
FIG. 3 shows a schematic representation of a tool with a working end determination device according to a third configuration example of the present invention.

As a third configuration example, FIG. 3 also illustrates an embodiment with readable data memory, in which the RFID device is housed in a ring body 60 that is fixedly, for example in a latching manner, attached to the tool 10 or slidably movable over it at the end portion of the shaft section/tool shaft or handle section 30 remote from the distal working end. In the third configuration example, the RFID device with antenna (not shown) and transponder electronics (not shown) is housed in, for example, the volume of the ring body 60. For fluid-tight and gas-tight design of the ring body 60, the ring body 60 may preferably be produced as an overmolded and/or molded assembly made of, for example, a plastic material or the like. Furthermore, the antenna of the RFID device may be formed in a coil shape in the annular space of the ring body 60.

Figure 3A:
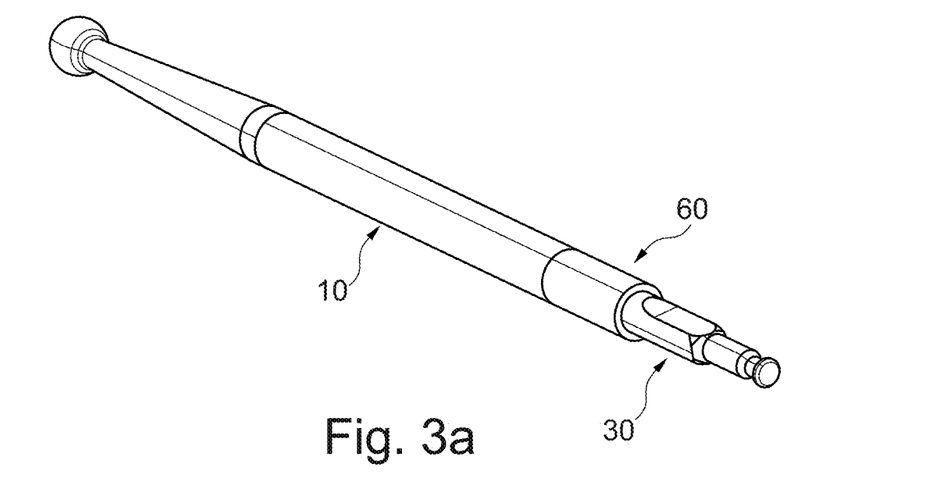
FIG. 3a shows a schematic representation of the tool of FIG. 3 with the working end determination device in another configuration.
Figure 3B:
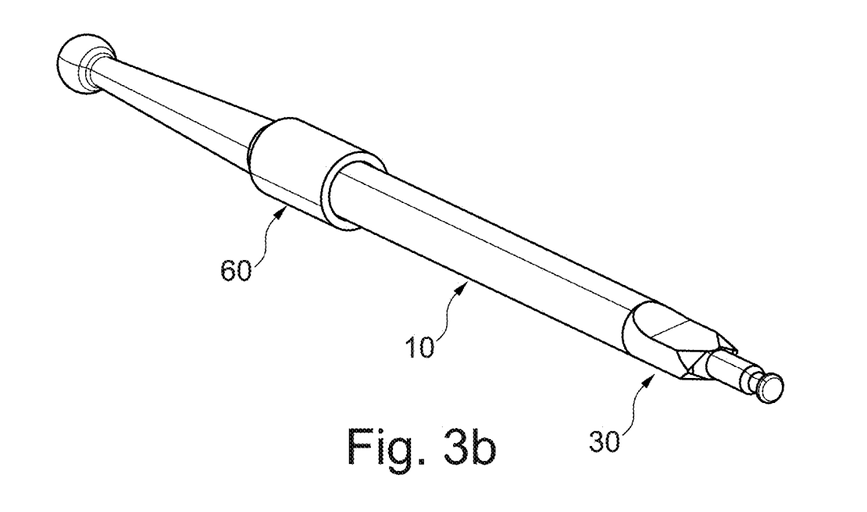
FIG. 3b shows a schematic representation of the tool of FIG. 3 with the working end determination device in another configuration.

In addition to the preceding FIG. 3, reference is also made to FIGS. 3a and 3b. In these further figures, the medical tool 10 of FIG. 3 is shown in which the ring body 60 already known from FIG. 3 is mounted at different axial positions of the tool shaft for receiving the RFID device. For example, it is possible to mount the ring body 60 immediately distal to the non-circular, proximal insertion end portion of the tool 10 or in a central portion of the tool shaft. Also, FIGS. 3a and 3b show that the ring body 60 according to FIG. 3 can vary at least with respect to its axial dimensions in order to be adapted as optimally as possible to the dimensions of the RFID device received therein.

Figure 4:
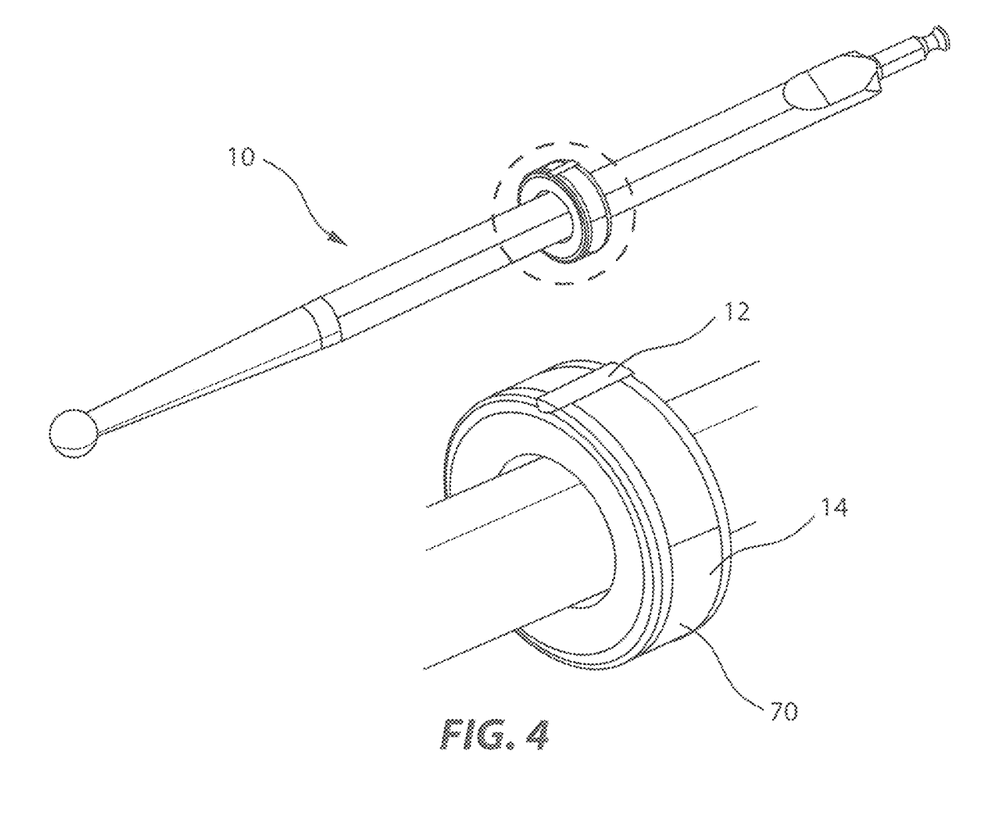
FIG. 4 shows a schematic representation of a tool with a working end determination device according to a fourth configuration example of the present invention.

As a fourth configuration example, FIG. 4 also depicts an embodiment with a readable data memory, in which the RFID device is housed on an outer ring of a bearing device 70, for example a ball bearing, which is preferably arranged in a fixed manner along the shaft section. In the fourth configuration example, the RFID device with antenna and transponder electronics is housed, for example, in a recess along the periphery of the bearing device 70, wherein, in particular, the installed readable data memory 12 can be embedded on the outer ring and, at the same time, sufficient space remains for a coil-shaped antenna 14 that is also embedded in the outer ring. For the fluid-tight and gas-tight design of the outer ring space, it can preferably be cast with, for example, a plastic material or the like. It can be particularly advantageous in this configuration example that the RFID device remains rotation-free, since the outer ring of the bearing device 70 is firmly positioned in a corresponding counterpart of a surrounding mounting or housing arrangement.

Figure 5:
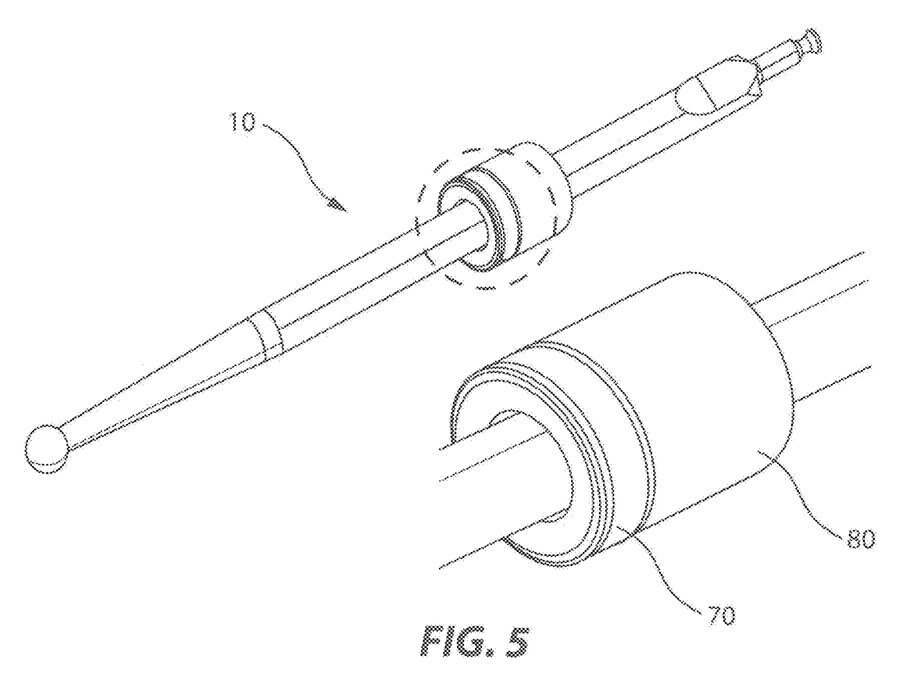
FIG. 5 shows a schematic representation of a tool with a working end determination device according to a fifth configuration example of the present invention.

As a fifth configuration example, FIG. 5 also shows an embodiment with a readable data memory, in which the RFID device is housed in a spacer sleeve element 80, for example of the bearing device 70, which is preferably fixedly installed along the shaft section, wherein the spacer sleeve is used as a carrier for the RFID/NFC chip. In this configuration example, sufficient installation space is provided as well in order to include an antenna, so that in this configuration example as well the RFID device with antenna and transponder electronics (not shown) can be housed in, for example, a space along the periphery of the spacer sleeve element 80, wherein in particular the installed readable data memory (not shown) can be embedded in an annular space section and at the same time sufficient space remains for the antenna (not shown), which is designed in the form of a coil and is also embedded in the annular space section. For fluid-tight and gas-tight design of the annular space section, it can preferably be cast with, for example, a resin or plastic material or the like. It can be particularly advantageous in this configuration example that the RFID device remains rotation-free when the spacer sleeve element 80 is firmly positioned in a corresponding counterpart of a surrounding mounting or housing arrangement.

Figure 6:
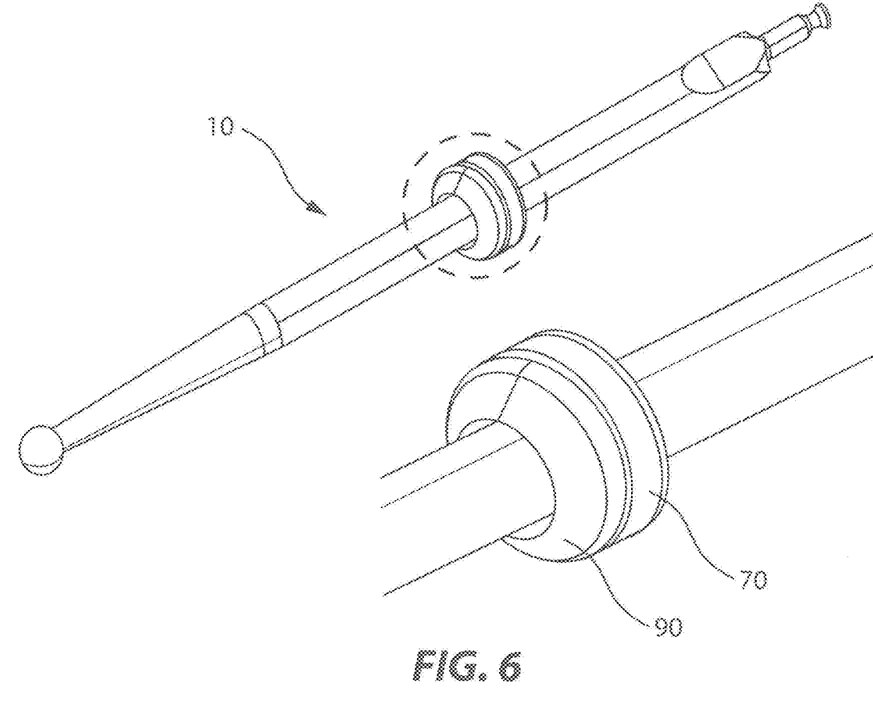
FIG. 6 shows a schematic representation of a tool with a working end determination device according to a sixth configuration example of the present invention.

As a sixth configuration example, FIG. 6 also illustrates an embodiment with readable data memory, in which the RFID device is housed in a splash guard element 90, for example of the bearing device 70, which is preferably fixedly installed along the shaft section, wherein the splash guard element 90 is used as a carrier for the RFID/NFC chip. In this configuration example, sufficient installation space is provided as well to include an antenna, so that in this configuration example as well, the RFID device with antenna (not shown) and transponder electronics (not shown) can be housed in, for example, a space along the periphery of the splash guard element 90, wherein in particular the installed readable data memory (not shown) can be embedded in an annular space section and, at the same time, sufficient space remains for the antenna (not shown), which is designed in the form of a coil and is also embedded in the annular space section. For fluid-tight and gas-tight design of the annular space section, it can preferably be cast with, for example, a resin or plastic material or the like. It can be particularly advantageous in this configuration example that the RFID device remains rotation-free when the splash guard element 90 is firmly positioned in a corresponding counterpart of a surrounding mounting or housing arrangement and/or is coupled in a torsion-resistant manner to, for example, a bearing device 70 or the like to be protected.

Figure 7:
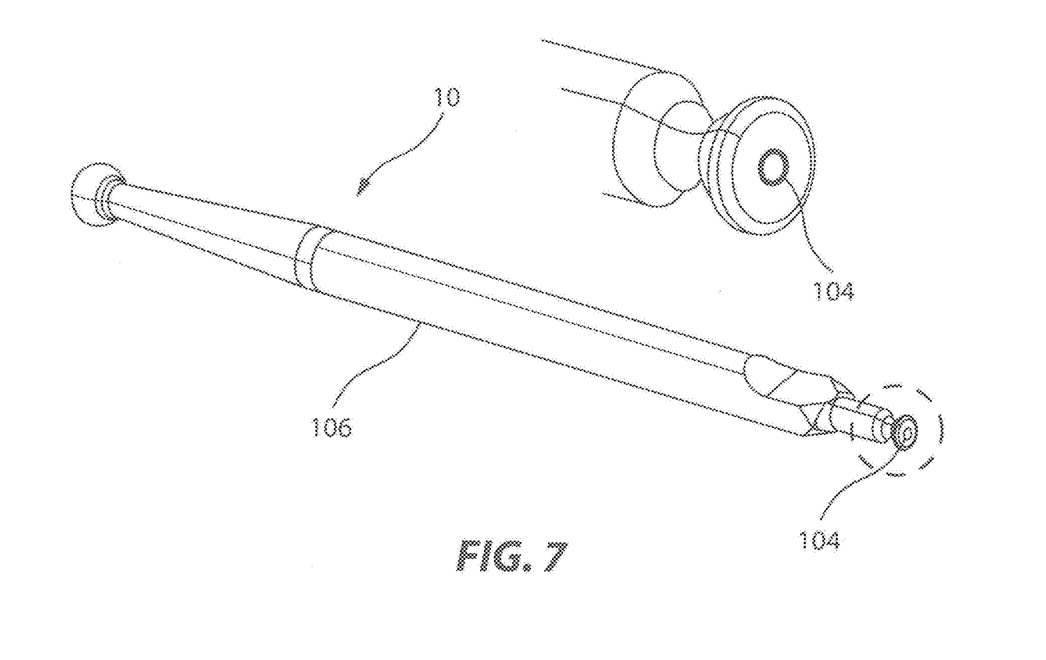
FIG. 7 shows a schematic representation of a tool with a working end determination device in an alternative embodiment according to a seventh configuration example of the present invention.
Figure 8:
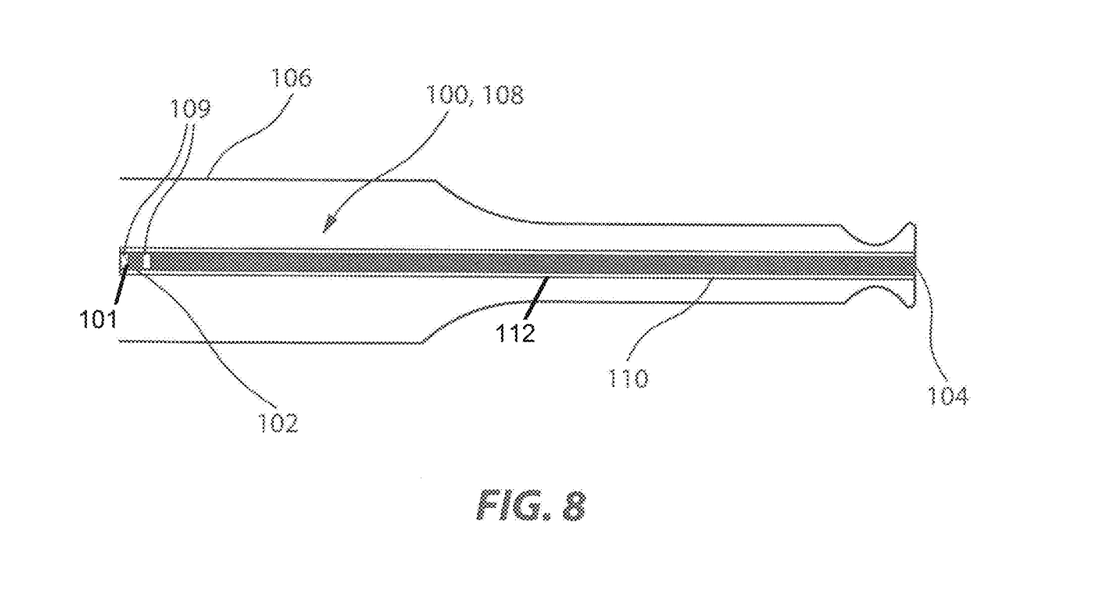
FIG. 8 shows a sectional view to illustrate a working end determination device formed in the tool as an integrated unit in the seventh configuration example.

FIGS. 7 and 8 show, in an alternative embodiment, as a seventh configuration example of the medical tool having a working end determining device arranged in the shaft portion thereof, a unit 100 integrated in the tool 10 forming the working end determining device, having a resistor 101 determining the working end of the tool, which may be, for example, an SMD resistor or the like, and/or a storage device storing data related to the working end, which may be, for example, an SMD memory chip or the like, 102, wherein the unit 100 integrated in the tool 10 is connectable to an external device (not shown), for example a control device or a signal and/or data processing device, via an electrical contact 104 in a handpiece 106 of the tool 10, said electrical contact 104 being led out of the unit 100.

To this end, in a sectional view through the proximal end portion 106 of the tool, FIG. 8 depicts in greater detail the arrangement of the integrated unit 100 in the tool 10. According to FIG. 8, the unit 100 integrated in the tool 10 extends into the tool with a channel-shaped structure 108 in the direction towards the distal working end, starting from a proximal end of the tool 10 on the handle side or shaft side, at which the electrical contact 104 is arranged on the outside of the tool. In the channel-shaped structure, at a first end facing the distal working end (e.g., milling head), the resistor 101 determining the working end (e.g., milling head) of the tool and/or the storage device 102 storing data related to the working end (e.g., milling head) is arranged, and the electrical contact 104 is arranged at a second end facing away from the distal working end. At least one conductive section electrically contacts the resistor 101 and/or the storage device 102. In the channel-shaped structure, contacts 109 connect the resistor 101 and/or the storage device 102 to a conductor 110 leading to the electrical contact 104 and to a potential-side ground, and the channel-shaped structure extends encased within an insulator 112 or insulating material that electrically insulates its interior components from the tool 10.

Figure 8A:
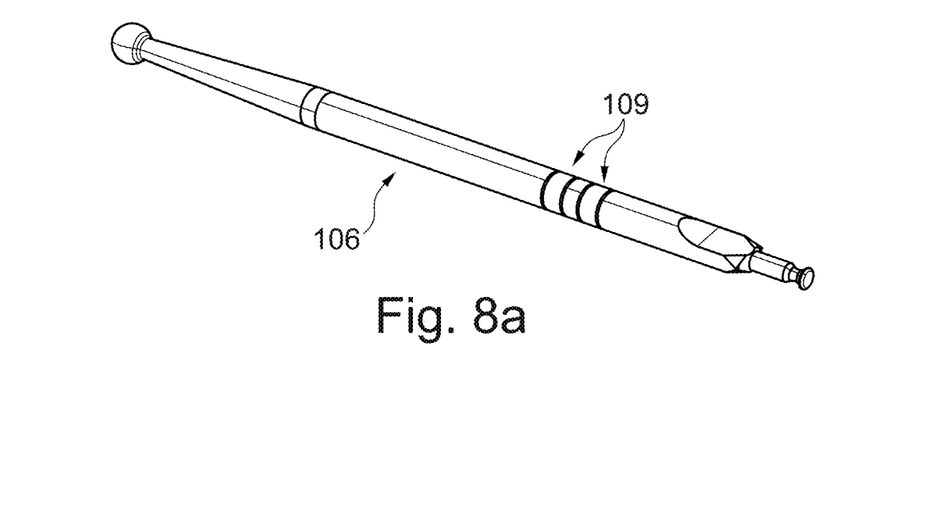
FIG. 8a shows a perspective view to illustrate another working end determination device formed in the tool as an integrated unit in the seventh configuration example.
Figure 8B:
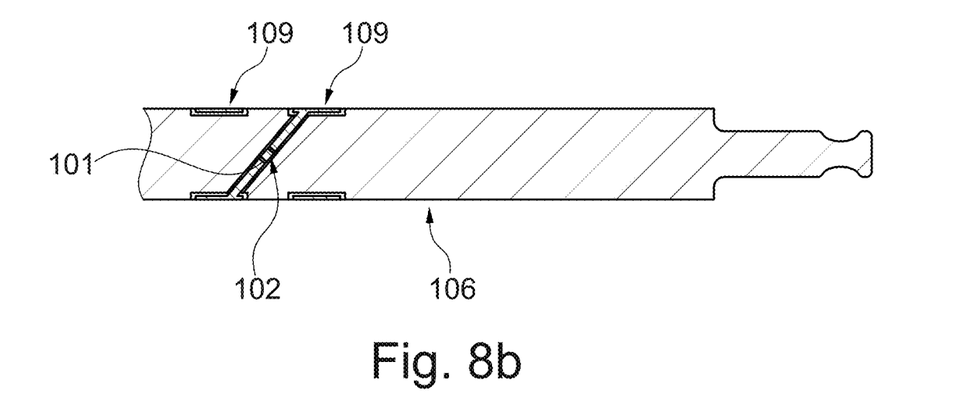

It should be noted at this point that the contacts 109 according to FIG. 8 are shown purely functionally as contact points or strips. FIGS. 8*a* and 8*b*, on the other hand, show a possible constructive design of these contacts 109 preferably as contact rings, which consequently can be held in contact abutment in any rotational position of the tool with respect to a tool accommodation on the side of a handle or a drive unit with contact pins (not shown) present there. In this case, the resistor 101 can be arranged inside the shaft and can have an electrical connection to the ring contacts via a line.

Figure 8C:
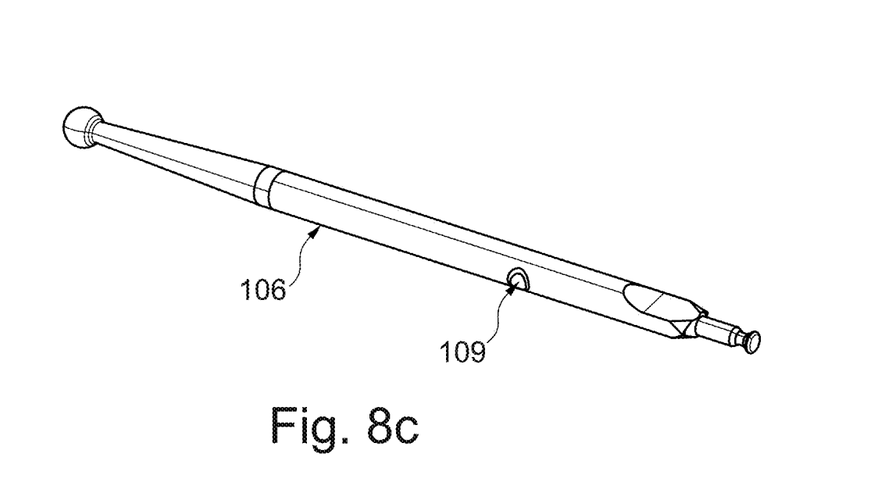
FIG. 8c shows a perspective view to illustrate another working end determination device formed in the tool as an integrated unit in the seventh configuration example.
Figure 8D:
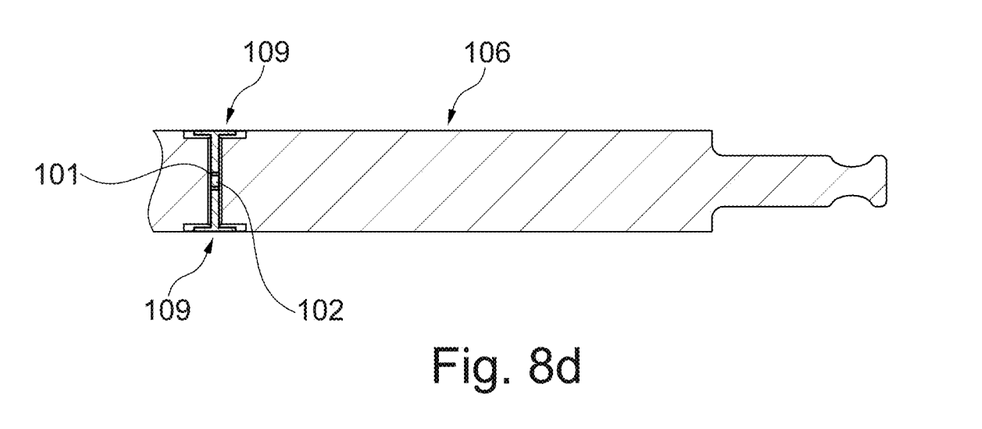
FIG. 8d shows a truncated cross-sectional view of the working end determination device of FIG. 8c.

An alternative construction of the contact points is shown in FIGS. 8*c* and 8*d*, according to which the contact points 109 are formed as two contact pads or contact surfaces arranged at shaft circumferential positions diametrically opposed to each other (i.e., opposite each other). These are electrically connected to each other via a transversely extending line into which a resistor 101 is interposed.

Advantageously, the writable and/or readable data storage device may include at least a second memory area configured to store data other than data related to the working end of the tool.

As has been described above, a tool 10 has a working end determination device 20 disposed in a shaft region thereof for determining and/or recognizing a working end of the tool 10, wherein the working end determination device 20 includes a writable and/or readable data storage device 12 configured to store at least data related to the working end of the tool in at least a first memory area, and wherein the working end determination device is arranged to provide the data related to the working end of the tool in an externally detectable manner for recognizing the working end of the tool. The working end determination device may be an RFID device comprising at least the data storage device and an antenna device. Alternatively, it can be a unit integrated into the tool, which can be connected to an external control device via an electrical contact in a handpiece region of the tool, wherein the unit integrated into the tool comprises a resistor determining the working end of the tool and/or a storage device storing data related to the working end. Thus, working ends can be detected and, depending on the embodiment variant, data previously written on the readable data memory can also be read out and used further.

It is understood that the invention is not limited to the preceding configuration example, but that changes, modifications and equivalent arrangements within the scope of protection defined according to the claims are also covered by the invention. For example, pay-per-use applications and consignment stock approaches are conceivable as applications for which such changes, modifications and equivalent arrangements are readily apparent to the person skilled in the art.

The invention claimed is:

1. A tool comprising a resistor and a writable and/or readable data storage device arranged in a shaft region of the tool for identifying a working end of the tool, wherein the resistor is configured to identify the working end of the tool and the writable and/or readable data storage device is configured to store data related to the working end of the tool in at least a first memory area, and wherein the resistor and the writable and/or readable data storage device are arranged to provide the data related to the working end of the tool in an externally detectable manner for recognizing the working end of the tool, wherein the resistor and the writable and/or readable data storage device are integrated as a unit into the tool and connectable to an external control device via an electrical contact in the shaft region, wherein the unit comprises a channel structure that extends into the tool from an end of the tool on a handle side or shaft side toward the working end of the tool, wherein the resistor and/or the writable and/or readable data storage device is arranged in the channel structure at a first end of the channel structure facing the working end of the tool, and wherein the electrical contact is arranged at a second end of the channel structure facing away from the working end of the tool, wherein at least one conductive section makes electrical contact with the resistor and/or the storage device, and wherein the channel-shaped structure is enclosed by an insulator and is electrically insulated by the insulator with respect to the tool.

2. The tool according to claim 1, wherein the writable and/or readable data storage device includes at least one second memory area configured to store predetermined data other than the data related to the working end of the tool.

3. A tool comprising a resistor and a writable and/or readable data storage device arranged in a shaft region of the tool for identifying a working end of the tool, wherein the resistor is configured to identify the working end of the tool and the writable and/or readable data storage device is configured to store data related to the working end of the tool in at least a first memory area, and wherein the resistor and the writable and/or readable data storage device are arranged to provide the data related to the working end of the tool in an externally detectable manner for recognizing the working end of the tool, wherein the resistor and the writable and/or readable data storage device are integrated as a unit into the tool and connectable to an external control device via an electrical contact in the shaft region;

wherein the shaft region of the tool comprises a proximal end for insertion into a handle or handpiece and a distal end comprising the working end of the tool;

wherein the electrical contact is located at the proximal end of the shaft region on the outside of the tool; and wherein the tool further comprises a conductor that extends from the proximal end to the resistor and the writable and/or readable data storage device.

4. The tool according to claim 3, wherein the writable and/or readable data storage device includes at least one second memory area configured to store predetermined data other than the data related to the working end of the tool.

5. The tool according to claim 3, wherein the resistor and the writable and/or readable data storage device are connected to the conductor, and the conductor is connected to the electrical contact.

6. The tool according to claim 5, wherein the conductor is encased in an insulator that extends to the proximal end of the shaft region.

7. The tool according to claim 3, wherein the writable and/or readable data storage device includes at least one second memory area configured to store predetermined data other than the data related to the working end of the tool.

8. A tool comprising a working end determination device arranged in a shaft region of the tool for identifying a working end of the tool, the working end determination device consisting of a resistor, a data storage device that is writable and/or readable, and an electrical connection, wherein the resistor is configured to identify the working end of the tool and the data storage device is configured to store data related to the working end of the tool in at least a first memory area, and wherein the resistor and the data storage device are arranged to provide the data related to the working end of the tool in an externally detectable manner for recognizing the working end of the tool, wherein the working end determination device is integrated as a unit into the tool and connectable to an external control device via an electrical contact in the shaft region.

9. The tool according to claim 8, wherein the writable and/or readable data storage device includes at least one second memory area configured to store predetermined data other than the data related to the working end of the tool.

* * * * *